(12) United States Patent
Ma et al.

(10) Patent No.: US 8,588,888 B2
(45) Date of Patent: Nov. 19, 2013

(54) CT AND MRI SYNCHRONOUS DETECTION POSITIONING NEEDLE

(75) Inventors: Dedong Ma, JiNan (CN); Wei Xiao, JiNan (CN); Qingshi Zeng, JiNan (CN); Ying Xing, JiNan (CN); Hongxiu Lu, JiNan (CN)

(73) Assignee: Shandong University, Jian City (CN)

( * ) Notice: Subject to any disclaimer, the term of this patent is extended or adjusted under 35 U.S.C. 154(b) by 40 days.

(21) Appl. No.: 13/377,044

(22) PCT Filed: Apr. 25, 2011

(86) PCT No.: PCT/CN2011/000716
§ 371 (c)(1),
(2), (4) Date: Dec. 8, 2011

(87) PCT Pub. No.: WO2012/092692
PCT Pub. Date: Jul. 12, 2012

(65) Prior Publication Data
US 2012/0179025 A1 Jul. 12, 2012

(30) Foreign Application Priority Data
Jan. 6, 2011 (CN) .......................... 2011 1 0001927

(51) Int. Cl.
*A61B 5/055* (2006.01)
*A61B 6/00* (2006.01)

(52) U.S. Cl.
USPC ........................... 600/411; 600/420; 600/431

(58) Field of Classification Search
USPC .......... 600/411, 414, 420, 431, 432; 382/128, 382/131; 128/899; 606/130
See application file for complete search history.

(56) References Cited

U.S. PATENT DOCUMENTS

| 5,713,828 A | 2/1998 | Coniglione |
| 6,419,680 B1 | 7/2002 | Cosman et al. |
| 2008/0317312 A1 | 12/2008 | Carl et al. |
| 2009/0196470 A1 | 8/2009 | Carl et al. |
| 2009/0217932 A1 | 9/2009 | Voegele |

FOREIGN PATENT DOCUMENTS

| CN | 101374570 A | 2/2009 |
| CN | 101513357 A | 8/2009 |
| CN | 101524290 A | 9/2009 |
| CN | 201591856 U | 9/2010 |
| CN | 102008315 A | 4/2011 |
| JP | A-63-294838 | 12/1988 |

OTHER PUBLICATIONS

International Search Report dated Sep. 15, 2011 in International Application No. PCT/CN2011/000716 (with translation).
Written Opinion of the International Searching Authority dated Sep. 15, 2011 in International Application No. PCT/CN2011/000716 (with partial translation).

*Primary Examiner* — Michael Rozanski
(74) *Attorney, Agent, or Firm* — Oliff & Berridge, PLC

(57) ABSTRACT

Disclosed is a CT and MRI synchronous detection positioning needle. The needle comprises a silicone tube which is internally provided with a guide needle; the two sides of the guide needle are provided with hollow cavities; each hollow cavity is internally provided with membranes dividing the hollow cavity into a plurality of small chambers which are filled with liquid, wherein a CT contrast agent is filled in a plurality of small chambers at one side of the guide needle, and an MRI contrast agent is filled in a plurality of small chambers at the other side of the guide needle. In the invention, specially designed silicone positioning needles are implanted in vivo, and synchronous comparison of different image data and pathological data is implemented by means of multi-plane reconstruction technology, so the CT and MRI synchronous detection positioning needle can be widely applied to experimental study on tumors.

5 Claims, 1 Drawing Sheet

CT AND MRI SYNCHRONOUS DETECTION POSITIONING NEEDLE

BACKGROUND

1. Field of Invention

The present invention relates to a CT and MRI synchronous detection positioning needle.

2. Description of Related Art

At present, with the development of functional imaging, CT and MRI can measure more and more functional indexes, such as blood perfusion parameters and parameters reflecting oxygen supply conditions. In order to achieve one-to-one correspondence with a histopathological section or immunohistochemical section image to accurately evaluate the effect of functional imaging in practical application, a reliable synchronous positioning device and method are required.

SUMMARY

Aiming at the prior art discussed above, the present invention provides a CT and MRI synchronous detection positioning needle.

The present invention is implemented by the technical scheme as follows:

A CT and MRI synchronous detection positioning needle comprises a silicone tube which is internally provided with a guide needle, the two sides of the guide needle are provided with hollow cavities, each hollow cavity is internally provided with membranes dividing the hollow cavity into a plurality of small chambers which are filled with liquid, wherein a CT contrast agent is filled in a plurality of small chambers at one side of the guide needle, an MRI contrast agent is filled in a plurality of small chambers at the other side of the guide needle, and the silicone tube covering each small chamber is differently colored.

The number of the small chambers filled with the CT contrast agent is 5 to 20, and the number of the small chambers filled with the MRI contrast agent is identical to that of the small chambers filled with the CT contrast agent. The concentrations of the contrast agent in the small chambers can be determined according to conditions and requirements.

Preferably, the number of the small chambers filled with the CT contrast agent is 10, wherein the concentrations (iodine concentration) of the CT contrast agent filled in the small chambers are successively as follows: 300 mg/ml, 150 mg/ml, 75 mg/ml, 40 mg/ml, 20 mg/ml, 10 mg/ml, 5 mg/ml, 2.5 mg/ml, 1.25 mg/ml and 0.625 mg/ml; and correspondingly, the number of the small chambers filled with the MRI contrast agent is also 10, wherein the concentrations of the MRI contrast agent filled in the small chambers are successively as follows: 0.5 mol/L, 0.25 mol/L, 0.125 mol/L, 0.0625 mol/L, 0.03125 mol/L, 0.02 mol/L, 0.01 mol/L, 0.005 mol/L, 0.0025 mol/L and 0.00125 mol/L.

The outer edge of the silicone tube is provided with at least one gap, thus facilitating identification.

When a plurality of positioning needles are needed, the needles with different number of the gaps can be selected for distinction.

The small chambers filled with the CT contrast agent are different from the small chambers filled with the MRI contrast agent in the color of the silicone wall, thus facilitating distinction.

During preparation, the CT contrast agent and the MRI contrast agent are filled into the small chambers in advance, and the small chambers are then sealed.

When in use, after a tumor-bearing animal is anesthetized, 2 to 3 positioning needles are inserted into the tumor based on precision requirement, and the guide needles are removed, so CT or MRI scanning imaging can be performed as required, the positioning needles are shown on tomographic images as markers indicating gradient change of signal intensity, relative positions of CT imaging and MRI imaging can be found in accordance with corresponding signal intensity, and therefore, image overlapping (or fusion) can be conducted; after an animal is killed, the tumor tissue is taken out, and after the tumor tissue is subjected to routine histopathological sectioning, the silicone walls corresponding to the small chambers filled with the CT contrast agent or the MRI contrast agent show different colors, therefore, relative positions of pathological sections and CT or MRI scanning results can be found.

In the invention, the specially designed silicone positioning needles are implanted in vivo, and synchronous comparison of different image data and pathological data is implemented by means of multi-plane reconstruction technology, so the CT and MRI synchronous detection positioning needle can be widely applied to experimental study on tumors.

The numbers in the figures respectively represent the following structures: 1. silicone tube; 2. guide needle; 3. hollow cavity; 4. gap; 5. membrane; 6. small chamber.

DETAILED DESCRIPTION

Further description is made below to the present invention with reference to the drawings and the embodiments.

Figure 1:
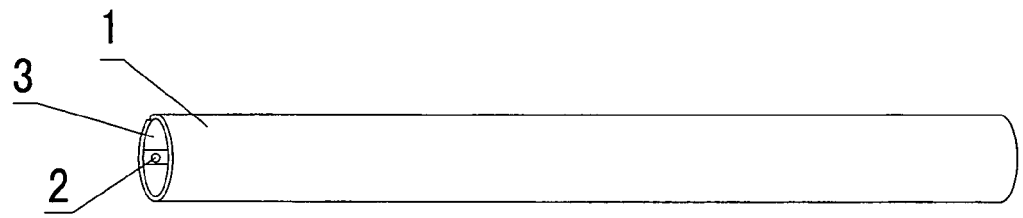
FIG. 1 is a structural schematic diagram of the present invention.
Figure 2:
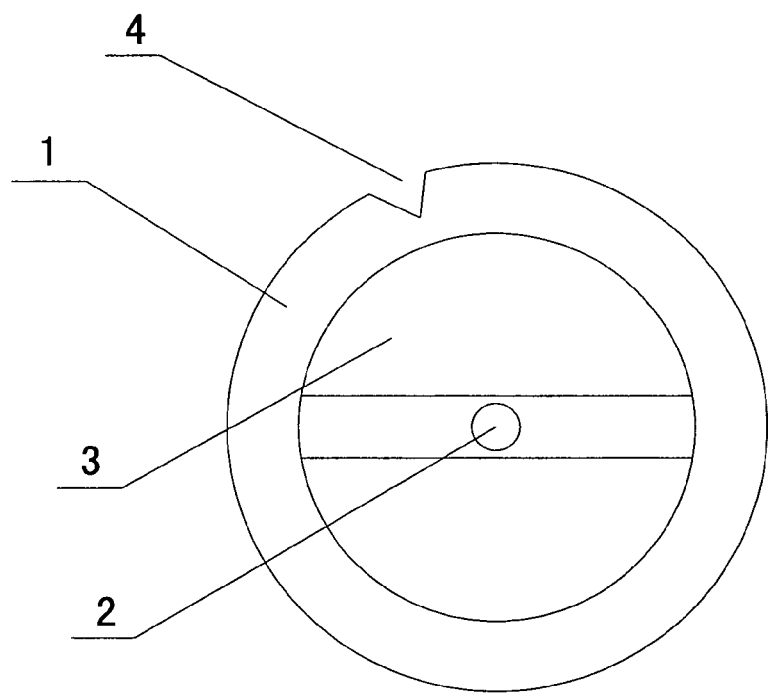
FIG. 2 is a structural schematic diagram of the cross section of the present invention.
Figure 3:
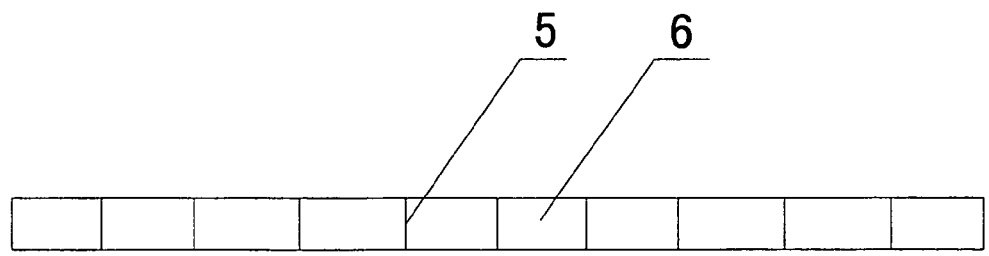
FIG. 3 is a structural schematic diagram of the longitudinal section of the present invention.

A CT and MRI synchronous detection positioning needle comprises a silicone tube 1; the silicone tube 1 is internally provided with a guide needle 2; shown as FIG. 1, FIG. 2 and FIG. 3, the two sides of the guide needle 2 are provided with hollow cavities 3, each hollow cavity 3 is internally provided with membranes 5 dividing the hollow cavity 3 into a plurality of small chambers 6 which are filled with liquid, wherein a CT contrast agent is filled in a plurality of small chambers 6 at one side of the guide needle 2, and an MRI contrast agent is filled in a plurality of small chambers 6 at the other side of the guide needle 2.

The number of the small chambers filled with the CT contrast agent is 10, shown as FIG. 3, wherein the concentrations (iodine concentration) of the CT contrast agent filled in the small chambers are successively as follows: 300 mg/ml, 150 mg/ml, 75 mg/ml, 40 mg/ml, 20 mg/ml, 10 mg/ml, 5 mg/ml, 2.5 mg/ml, 1.25 mg/ml and 0.625 mg/ml; and correspondingly, the number of the small chambers filled with the MRI contrast agent is also 10, wherein the concentrations of the MRI contrast agent filled in the small chambers are successively as follows: 0.5 mol/L, 0.25 mol/L, 0.125 mol/L, 0.0625 mol/L, 0.03125 mol/L, 0.02 mol/L, 0.01 mol/L, 0.005 mol/L, 0.0025 mol/L and 0.00125 mol/L.

The outer edge of the silicone tube is provided with at least one gap, thus facilitating identification.

During preparation, the CT contrast agent and the MRI contrast agent are filled into the small chambers in advance, and the small chambers are then sealed.

When in use, after a tumor-bearing animal is anesthetized, 2 to 3 positioning needles are inserted into the tumor based on precision requirement, and the guide needles are removed, so CT or MRI scanning imaging can be performed as required, the positioning needles are shown on tomographic images as markers indicating gradient change of signal intensity, relative positions of CT imaging and MRI imaging can be found in accordance with corresponding signal intensity, and therefore, image overlapping (or fusion) can be conducted; after an animal is killed, the tumor tissue is taken out, and after the tumor tissue is subjected to routine histopathological sectioning, the silicone walls corresponding to the small chambers filled with the CT contrast agent or the MRI contrast agent show different colors, therefore, relative positions of pathological sections and CT or MRI scanning results can be found.

In the invention, the specially designed silicone positioning needles are implanted in vivo, and synchronous comparison of different image data and pathological data is implemented by means of multi-plane reconstruction technology, so the CT and MRI synchronous detection positioning needle can be widely applied to experimental study on tumors.

What is claimed is:

1. A CT and MRI synchronous detection positioning needle comprising a silicone tube which is internally provided with a guide needle, wherein:
   the two sides of the guide needle are provided with hollow cavities,
   each hollow cavity is internally provided with membranes dividing the hollow cavity into a plurality of small chambers which are filled with liquid,
   a CT contrast agent is filled in a plurality of small chambers at one side of the guide needle, and
   an MRI contrast agent is filled in the plurality of small chambers at the other side of the guide needle.

2. The CT and MRI synchronous detection positioning needle according to claim 1, wherein the number of the small chambers filled with the CT contrast agent is 5 to 20, and the number of the small chambers filled with the MRI contrast agent is identical to that of the small chambers filled with the CT contrast agent.

3. The CT and MRI synchronous detection positioning needle according to claim 2, wherein the number of the small chambers filled with the CT contrast agent is 10, wherein the concentrations of the CT contrast agent filled in the small chambers are successively as follows: 300 mg/ml, 150 mg/ml, 75 mg/ml, 40 mg/ml, 20 mg/ml, 10 mg/ml, 5 mg/ml, 2.5 mg/ml, 1.25 mg/ml and 0.625 mg/ml; and correspondingly, the number of the small chambers filled with the MRI contrast agent is also 10, wherein the concentrations of the MRI contrast agent filled in the small chambers are successively as follows: 0.5 mol/L, 0.25 mol/L, 0.125 mol/L, 0.0625 mol/L, 0.03125 mol/L, 0.02 mol/L, 0.01 mol/L, 0.005 mol/L, 0.0025 mol/L and 0.00125 mol/L.

4. The CT and MRI synchronous detection positioning needle according to claim 1, wherein an outer edge of the silicone tube is provided with at least one gap.

5. The CT and MRI synchronous detection positioning needle according to claim 1, wherein the small chambers filled with the CT contrast agent are different from the small chambers filled with the MRI contrast agent in the color of a silicone wall.

* * * * *